US012672887B2

(12) United States Patent
Dua

(10) Patent No.: US 12,672,887 B2
(45) Date of Patent: Jul. 7, 2026

(54) CLOT REMOVAL SYSTEM AND METHODS OF USE

(71) Applicant: Anahita Dua, Brookfield, WI (US)

(72) Inventor: Anahita Dua, Brookfield, WI (US)

( * ) Notice: Subject to any disclaimer, the term of this patent is extended or adjusted under 35 U.S.C. 154(b) by 1054 days.

(21) Appl. No.: 17/561,143

(22) Filed: Dec. 23, 2021

(65) Prior Publication Data

US 2022/0110646 A1 Apr. 14, 2022

Related U.S. Application Data

(63) Continuation of application No. PCT/US2020/040256, filed on Jun. 30, 2020.

(60) Provisional application No. 62/886,133, filed on Aug. 13, 2019, provisional application No. 62/869,062, filed on Jul. 1, 2019.

(51) Int. Cl.
*A61B 17/22* (2006.01)
*A61B 17/3207* (2006.01)
*A61B 17/32* (2006.01)

(52) U.S. Cl.
CPC ...... *A61B 17/22* (2013.01); *A61B 17/320725* (2013.01); *A61B 2017/22054* (2013.01); *A61B 2017/22067* (2013.01); *A61B 2017/22079*

(2013.01); *A61B 2017/22084* (2013.01); *A61B 2017/320012* (2013.01); *A61B 2017/320733* (2013.01)

(58) Field of Classification Search
CPC .............. A61B 17/22; A61B 17/32075; A61B 2017/22054; A61B 2017/22067; A61B 2017/22079; A61B 2017/22084; A61B 2017/320012; A61B 2017/320733; A61B 2017/22061; A61B 2217/005
See application file for complete search history.

(56) References Cited

U.S. PATENT DOCUMENTS 5,947,985 A * 9/1999 Imran ............ A61B 17/320725
606/113
2019/0216495 A1* 7/2019 Walzman ....... A61B 17/320725

* cited by examiner

*Primary Examiner* — James D Ponton
*Assistant Examiner* — John A Doubrava
(74) *Attorney, Agent, or Firm* — SLEMAN & LUND LLP

(57) ABSTRACT

A system for removing a blood clot includes a first catheter having an inner sheath, the sheath having an interior passage and a plurality of apertures for delivering a drug, and a second catheter having a hollow outer sheath sized to fit over the inner sheath, the second catheter having an agitating element to break apart or loosen the blood clot.

7 Claims, 10 Drawing Sheets

CLOT REMOVAL SYSTEM AND METHODS OF USE

CROSS-REFERENCE TO RELATED APPLICATIONS

This application is a continuation of International Application PCT/US2020/40256, filed Jun. 30, 2020, entitled "CLOT REMOVAL SYSTEM AND METHODS OF USE," which claims priority to U.S. Provisional Application Ser. No. 62/869,062, filed Jul. 1, 2019, and U.S. Provisional Application Ser. No. 62/886,133, filed Aug. 13, 2019, the contents of which are hereby incorporated by reference in their entirety as if fully set forth herein.

FIELD OF THE DISCLOSURE

The present disclosure relates to systems, devices and methods for clot removal. Specifically, the disclosure relates to a system to loosen and retrieve blood clots from vessels.

BACKGROUND OF THE DISCLOSURE

The present invention pertains generally to emboli collection and removal.

Blood thrombus, may form a clot in a patient vasculature. Sometimes such clots are harmlessly dissolved in the blood stream. Unfortunately, however, in some cases such clots may lodge in a blood vessel where they can partially or completely occlude the flow of blood. If the partially or completely occluded vessel feeds blood to sensitive tissue such as, the brain, lungs or heart, for example, serious tissue damage may result.

When symptoms of an occlusion are apparent, such as an occlusion resulting in a stroke, immediate action should be taken to reduce or eliminate resultant tissue damage. One approach is to treat a patient with clot dissolving drugs. These drugs, however, do not immediately dissolve the clot from the patient.

SUMMARY OF THE INVENTION

In some embodiments, a system for removing a blood clot includes a first catheter having an inner sheath, the sheath having an interior passage and a plurality of apertures for delivering a drug, and a second catheter having a hollow outer sheath sized to fit over the inner sheath, the second catheter having an agitating element to break apart or loosen the blood clot.

In some embodiments, a method of removing a blood clot includes introducing a first catheter into a vessel, the first catheter having an inner sheath, the sheath having an interior passage and a plurality of apertures for delivering a drug, and a balloon; and advancing a second catheter having a hollow outer sheath over the inner sheath, the second catheter having an agitating element to break apart or loosen the blood clot.

In some embodiments, a device for removing a blood clot extends between a proximal end and a distal end, and includes a central sheath having a sidewall and defining a plurality of apertures in the sidewall, a first balloon adjacent the distal end, a second balloon adjacent the proximal end, and at least one undulating wire coupled at one end to the central sheath, the at least one undulating wire having a plurality of peaks and valleys.

In some embodiments, includes undulating wires where pulling on each of the plurality of undulating wires flattens them and brings them closer to the central sheath, and/or wherein ones of the plurality of undulating wires are coupled together at a second end so that they may be collectively manipulated by a physician, and/or wherein the at least one undulating wire is coupled at a second end to the central sheath.

BRIEF DESCRIPTION OF THE DRAWINGS

Various embodiments of the presently disclosed devices and methods are shown herein with reference to the drawings, wherein.

It is to be appreciated that these drawings depict only some embodiments of the disclosure and are therefore not to be considered limiting of its scope.

DETAILED DESCRIPTION OF THE DISCLOSURE

Despite the various improvements that have been made to clot removal, conventional techniques suffer from some shortcomings as described above.

Figure 1A:
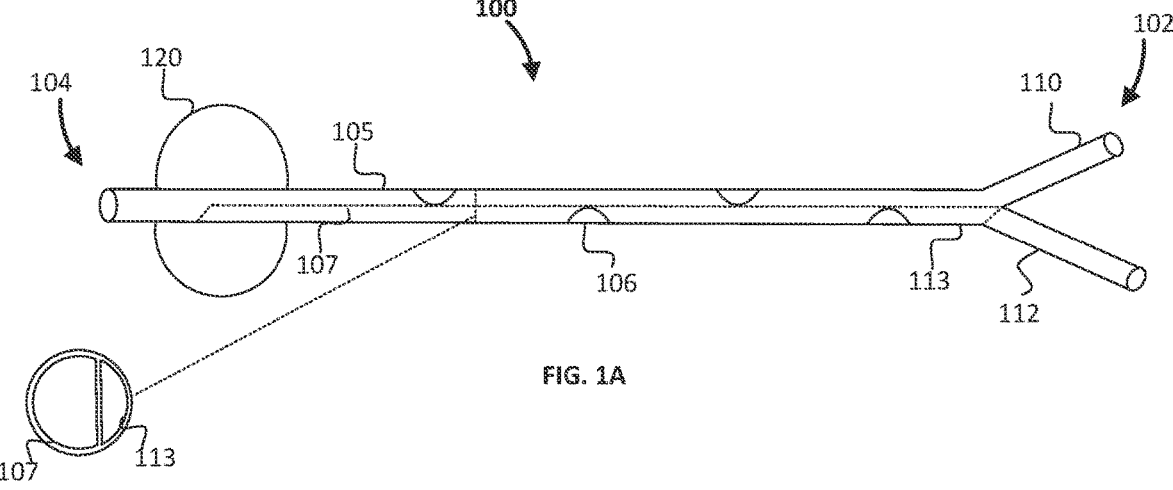
FIGS. 1A-C are schematic side views of one example of a balloon catheter, an agitating catheter, and the use of the two devices together, respectively.
Figure 1B:
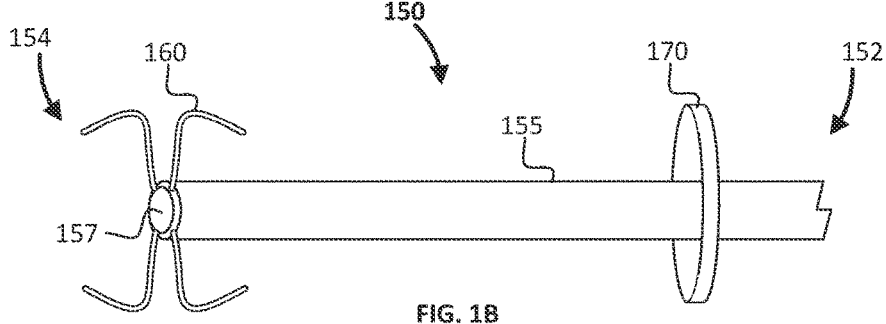
Figure 1C:
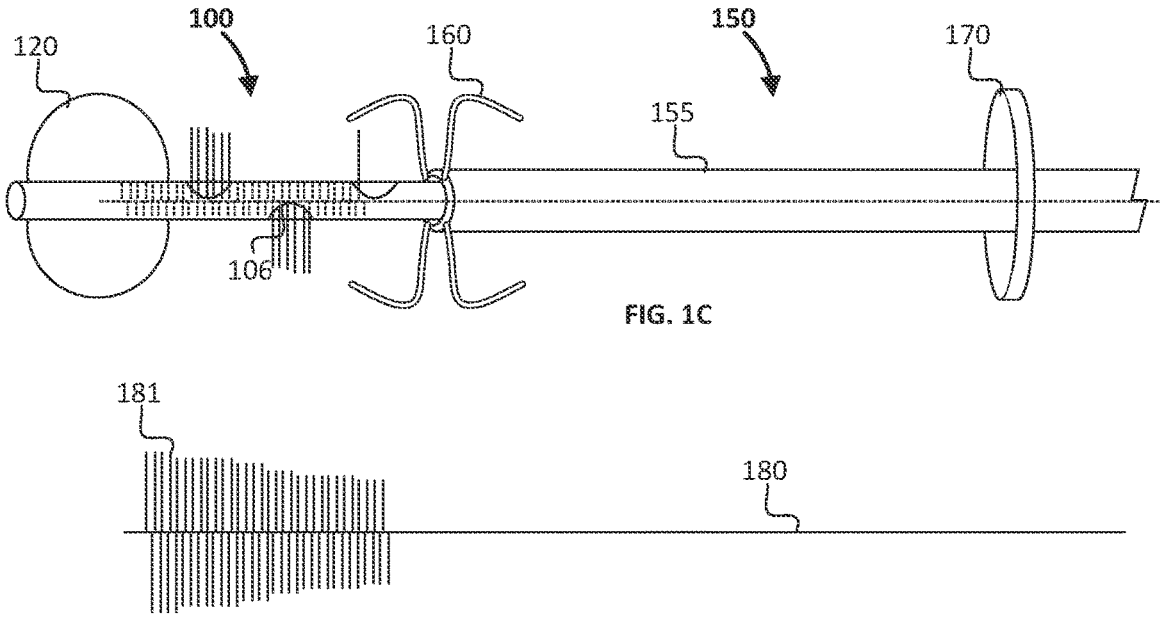

FIGS. 1A-C are schematic side views of a system of removing blood clots having two catheters. The system includes a first balloon catheter 100 extending between a proximal end 102 and a distal end 104. Balloon catheter 100 includes a first flexible sheath 105 configured and arranged to fit within the patient's vasculature. In at least some examples, sheath 105 is between 3 and 9 French and formed of a suitable biocompatible polymer or plastic. Sheath 105 may also include a plurality of apertures 106 defined in the sidewalls of the sheath, and may define a first lumen 107 extending between therethrough. Sheath 105 may be open adjacent the proximal end and along its length, and closed at one side adjacent a balloon to force material introduced through the lumen out through the sidewalls. Balloon catheter 100 may have a pair of ports, including a first TPA infusion and suction port 110, and a balloon inflation port 112. First port 110 may be used to infuse a drug, chemical or other therapy to the vasculature, such as tissue plasminogen activator (TPA), alteplase, heparin, saline, or any other medication or fluid solution that would assist in breakdown, irrigation or softening of the clot. First port 110 may also be in communication with a suction device (not shown) capable of drawing out blood clots. Second port 112 may be in communication with a secondary lumen 113 that extends along the body of the sheath and is in communication with balloon 120. Secondary lumen 113 may be independently and separately formed from lumen 107. In at least some examples the two lumens 107,113 are concentric with the secondary lumen 113 being disposed within the lumen 107. Alternatively, the two lumens 107,113 are disposed side-by-side.

A second agitating catheter 150 may be used in conjunction with the balloon catheter 100. Agitating catheter 150 may extend between proximal end 152 and distal end 154, and may include a sheath 155 having a central lumen 157. Central lumen 157 may be sized to accept and be delivered over at least a portion of sheath 105 of catheter 100. In at least some examples, central lumen 157 may be 0.18 inches to 1 inch. Disposed adjacent distal end 154 and extending radially are a plurality of agitating bristles 160. Bristles 160 may be formed of a plastic, metallic or alloy strand(s) such as nitinol or steel. Four bristles 140 are shown, although the number and spacing of the bristles may be adjusted as desired. In some embodiments, more than 6 bristles are used. In some embodiments, more than 10 bristles are used. Thus, multiple bristles may be utilized, the number of bristles varying as desired. Catheter 150 may also include an optional plug 170 in the form of a circular washer. Plug 170 may be sized or chosen to have a diameter approximately equal to or slightly smaller than that of the target vessels so that when deployed, no material (TPA, clots, etc.) is capable of passing beyond it toward the proximal end 152 of the catheter 150.

Optionally, an inner wire brush 180 may be used in addition to, or instead of bristles 140. Inner wire brush 180 may include a number of orthogonally extending bristles 181 similar to those of agitating catheter 150, the bristles 181 being formed of a metal or plastic (e.g., nitinol, steel, etc.). Inner wire brush 180 may be introduced through central lumen 157 and bristles 181 may be long enough to extend through apertures 106. With such a configuration, inner wire brush may be used to clean or scrap the inside of the central lumen to dislodged obstructions, or to further agitate clot material within the vessel by extending through the apertures 106.

Figure 1D:
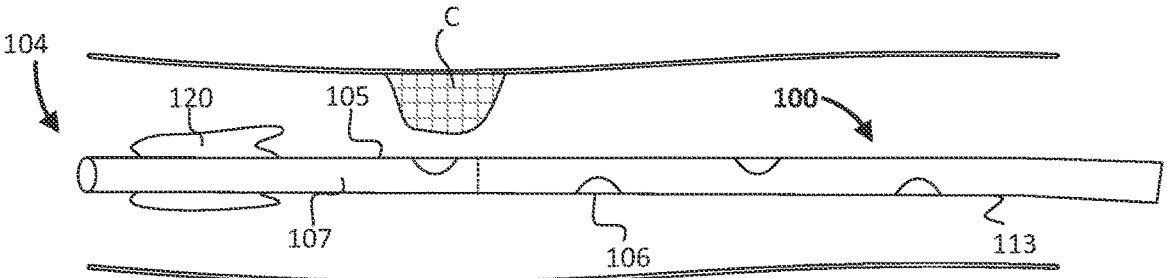
FIGS. 1D-H are schematic illustrations showing the use of the devices of FIGS. 1A-C.
Figure 1E:
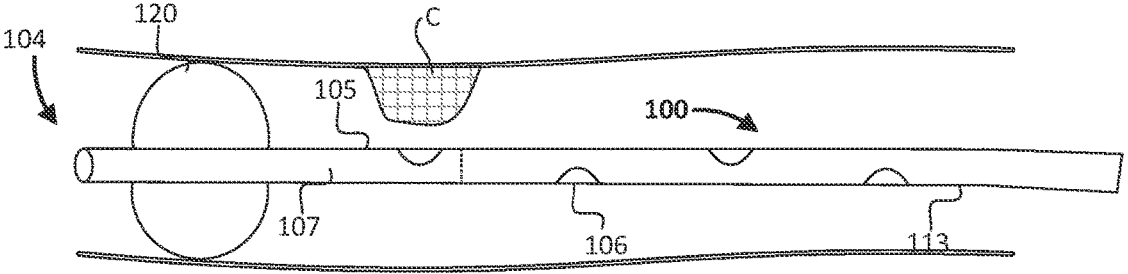
Figure 1F:
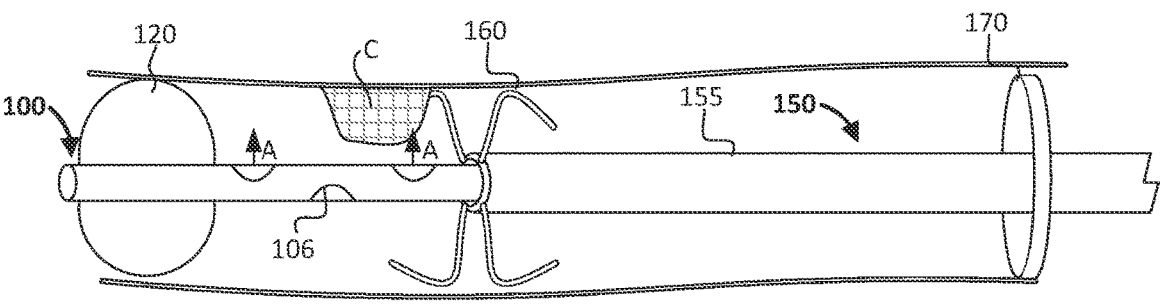
Figure 1G:
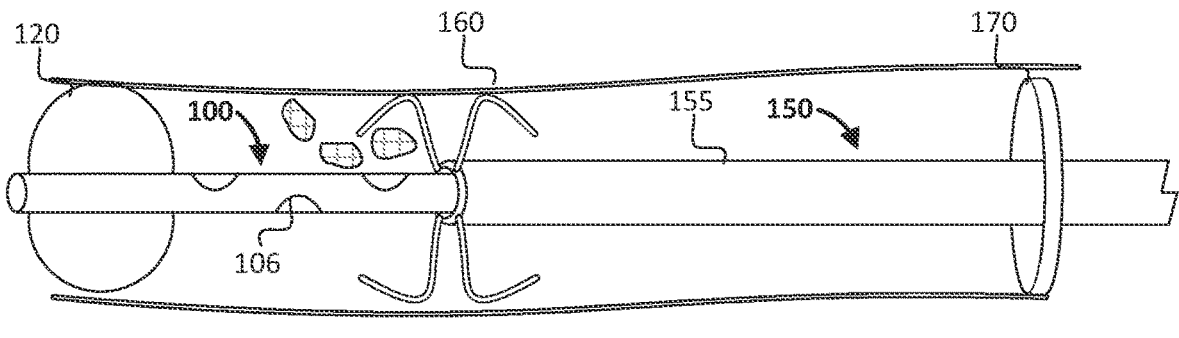
Figure 1H:
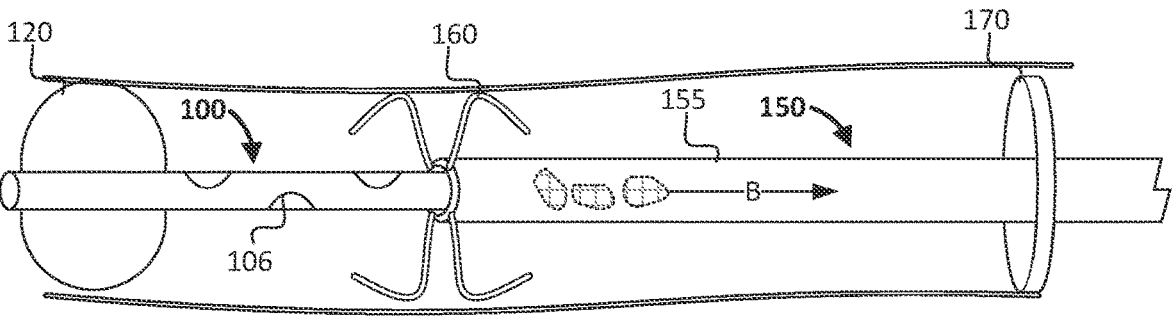

In use, the two catheters, 100,150 may be used together as part of a system. First, balloon catheter 100 may be introduced into the target vessel and passed beyond clot "C" (FIG. 1D). Balloon 120 may be inflated via inflation port (not shown) until the balloon contacts the walls of the vessel (FIG. 1E). With the balloon 120 in place, the agitating catheter 150 may be delivered over the sheath of the balloon catheter 100 until bristles 160 are disposed adjacent the clot "C". In some examples, agitating catheter 150 may be pre-mounted over catheter 100 so that the two catheters are assembled together one over the other. Plug 170 may create a secondary barrier opposite balloon 120 so that a defined work space is formed between the two elements with the clot "C" being disposed within the work space (FIG. 1F). TPA or other medication may be introduced through the balloon catheter and exit through apertures 106 in the direction of arrows "A" adjacent the clot "C". Bristles 160 may then be used to break up the clot "C" by moving the agitating catheter back-and-forth or rotating it. As the bristles break up the clot "C" into smaller fragments (FIG. 1G), a suction device may be used to vacuum the fragments through apertures 106 of balloon catheter 100 and out of the body in the direction of arrow "B" (FIG. 1H).

Figure 2A:
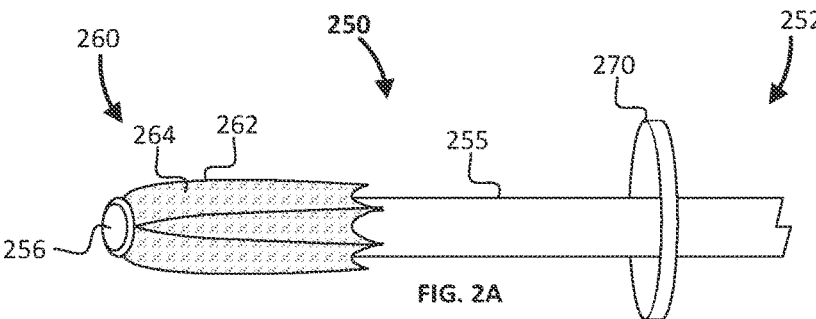
FIGS. 2A-C are schematic side views showing another example of an agitating catheter, and the use of the agitating catheter together with a balloon catheter, respectively.
Figure 2B:
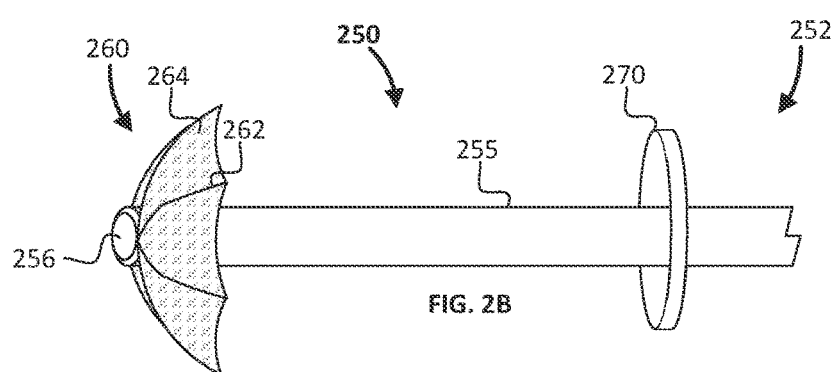
Figure 2C:
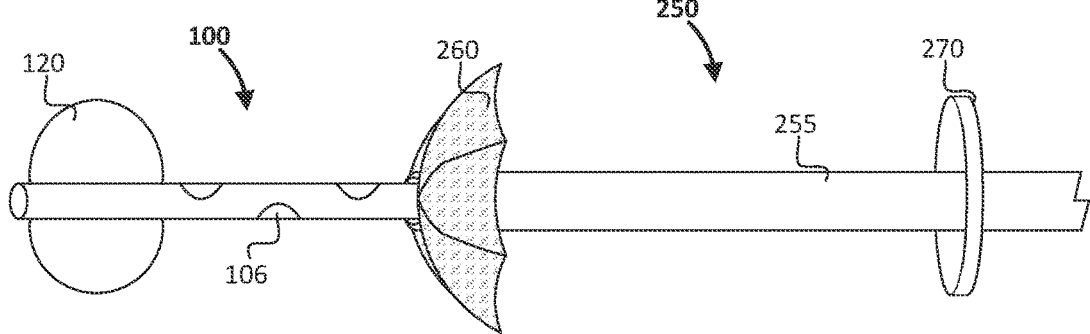

FIGS. 2A-C are schematic side views of an agitating catheter 250 according to another embodiment of the disclosure. Like-numbered elements of FIGS. 2A-C will be easily identified as being similar to those elements of FIG. 1, except that such elements will be preceded with "2" instead of "1". The main difference between agitating catheter 250 and agitating catheter 150 is that catheter 250 includes an umbrella-like agitating element 260 instead of bristles. Umbrella 260 may include a collapsible and expandable frame 262 with a covering 264 stretching over it that is capable of collapsing (FIG. 2A) and circumferentially expanding (FIG. 2B). Frame 262 may be formed of metallic wire or other suitable material, while covering 264 may be formed of a metallic mesh or fabric. As shown in FIG. 2C, sheath 255 of catheter 250 may be introduced over a balloon catheter as previously described, with the umbrella 260 being used to loosen and break apart clots in a manner similar to bristle 160.

Figure 3A:
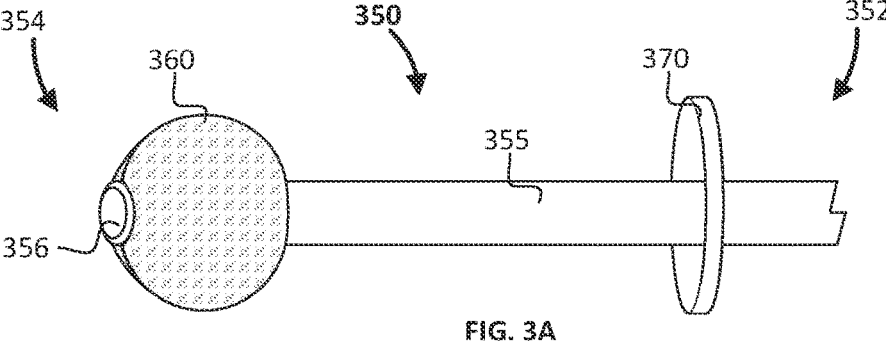
FIGS. 3A-B are schematic side views showing another example of an agitating catheter, and the use of the agitating catheter together with a balloon catheter, respectively.
Figure 3B:
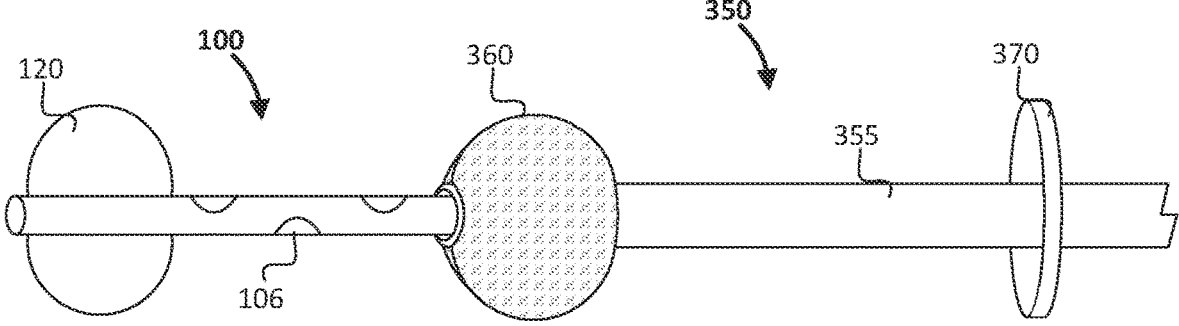

In yet another embodiment, shown in FIGS. 3A-B another agitating catheter is shown. Like-numbered elements of FIGS. 3A-B will be easily identified as being similar to those elements of FIG. 1, except that such elements will be preceded with "3" instead of "1". The main difference between agitating catheter 350 and agitating catheters 150, 250 is that catheter 350 includes a dome-like wire element 360 for scraping the clot instead of bristles or an umbrella. Dome 360 may be formed of metallic wire or other suitable material and may have a diameter slightly smaller than that of the target vessel. As shown in FIG. 3B, sheath 355 of catheter 350 may be introduced over a balloon catheter as previously described, with the dome 360 being used to loosen and break apart clots in a manner similar to the bristles and the umbrella previously described.

Figure 4A:
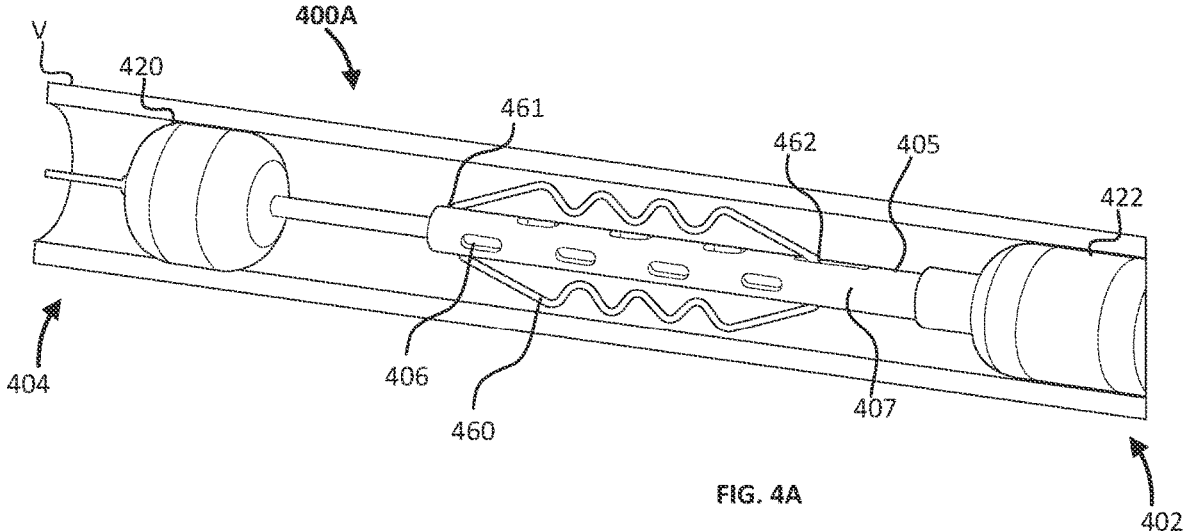
FIGS. 4A-B are schematic perspective views of other embodiments of an agitating catheter having an undulating wire.
Figure 4B:
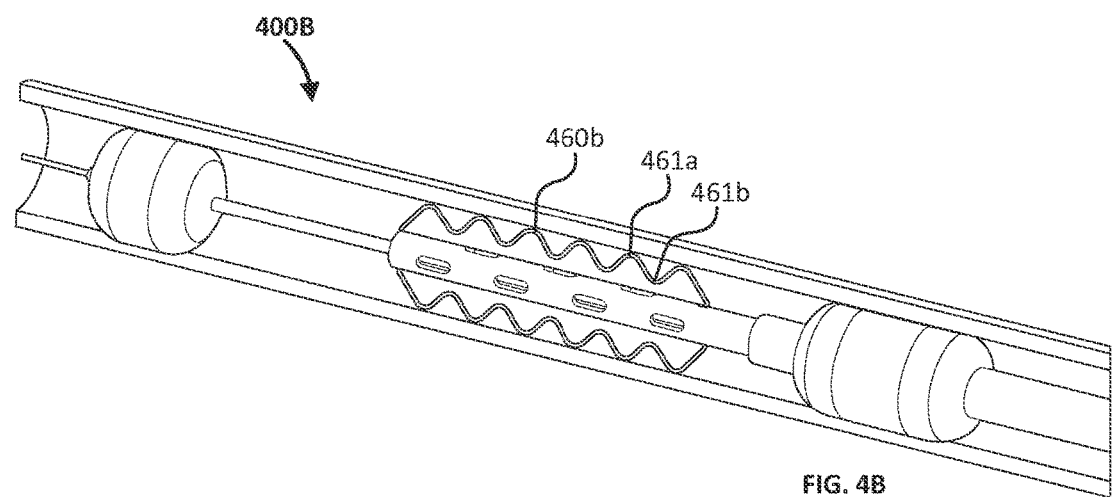

In another embodiment, shown in FIG. 4A, catheter 400A for use within a vessel "V" may include sheath 405 having a plurality of apertures 406. The sheath 406 may be similar to sheath 105 previously described and formed in the sizes described. Sheath 405 may include a plurality of apertures 406 defined in the sidewalls of the sheath, and may define a first lumen 407 extending between therethrough. Sheath 405 may be open adjacent the proximal end and along its length, and closed at one side adjacent a balloon to force material introduced through the lumen out through the sidewalls. Catheter 400A may have a number of ports to infuse a drug (e.g., TPA) through the apertures or to inflate either of balloons 420,422. In some examples, catheter 400A may have three ports (not shown) near its proximal end 402, one for each balloon and one for drug infusion through the apertures 406, and may have a lumen corresponding to each of the ports. In this embodiment, an integrated agitating element is presented in the form of a wire 460. Wire 460 may be coupled at a first end 461 to sheath 405 adjacent the distal end 404. Wire 460 may be coupled at a second end 462 to sheath 406 proximal to the first end. Alternatively, instead of being coupled at the second end, wire 460 may only be coupled at one end, and may extend through the sheath 405 and out of the catheter and the body to be manipulated by a physician. In such cases, the wire 460 may be collapsed within the body by pulling on the wire to flatten it or expanded by pushing it toward the attached first end. As shown, wire 460 may have an undulating or sinusoidal shape including a plurality of peaks and valleys. In one variation, shown in catheter 400B (FIG. 4B), the wire 460b may have a larger numbers of peaks 461a and valleys 461b so that it has more "teeth" than wire 460 for agitating a larger clot.

Two wires 460 are shown in these configurations, although more or less wires are possible (e.g., three, four or more wires), and the wires may be evenly distributed about the circumference of the sheath. Additionally, in embodiments where the wires are coupled to the sheath on one end and extend out of the catheter, they may be coupled together at the proximal end so that they are capable of collapsing and expanding together. Wires 460 may be formed of a plastic, metal or alloy such as nitinol or steel and may be used to agitate a clot similar to the bristles previously described. In at least some examples, wires 460 may be formed of a shape-memory material that may be stretched or flattened out and may return to their undulating shape when no external force is applied. In this manner, the wires may be delivered flat into the vessel by holding each at the proximal end, and may expand to their curved or undulating shapes when released from the proximal end to agitate a clot.

Figure 5:
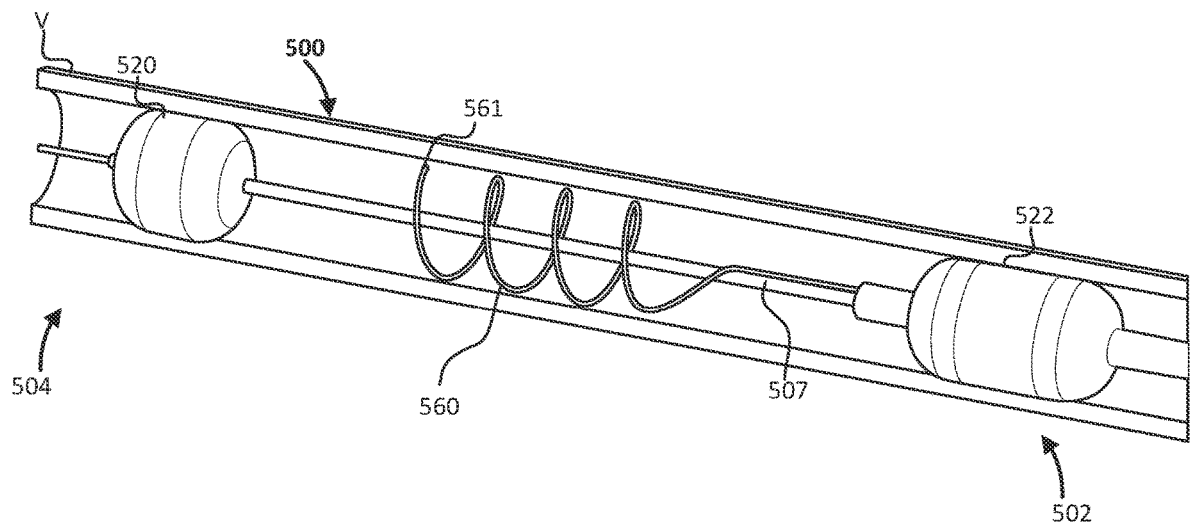
FIG. 5 is a schematic perspective view of another embodiment of an agitating catheter having a helical member.

In another embodiment, shown in FIG. 5, a catheter 500 for use within a vessel "V" may include a pair of balloons 520,522 and a helical wire 560 disposed about central tube 507. Central tube 507 may be used to inflate balloon 520. Optionally, another sheath or tube may be used to introduce a drug as described above. However, in this embodiment, the main difference is the presence of a helical wire having a free end 561 adjacent the distal end 504 of the catheter. Helical wire 560 may form one, two, three, four or more revolutions and may extend out the proximal end of the catheter for manipulation. Wire 560 may be formed of any of the materials previously described for agitating elements.

Figure 6:
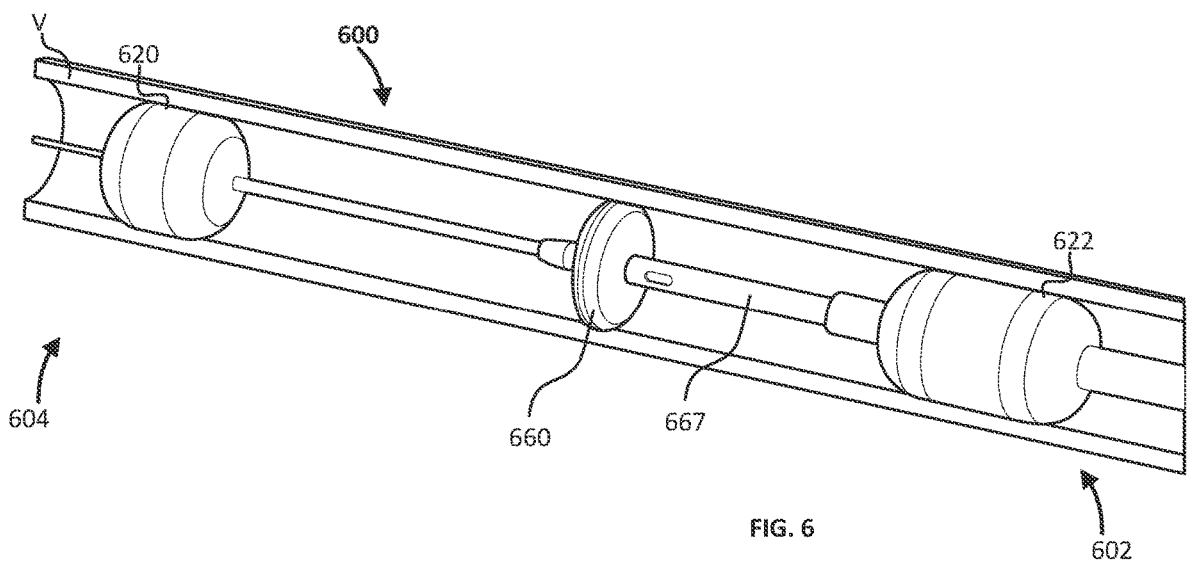
FIG. 6 is a schematic perspective view of another embodiment of an agitating catheter having an inflatable plug.
Figure 7A:
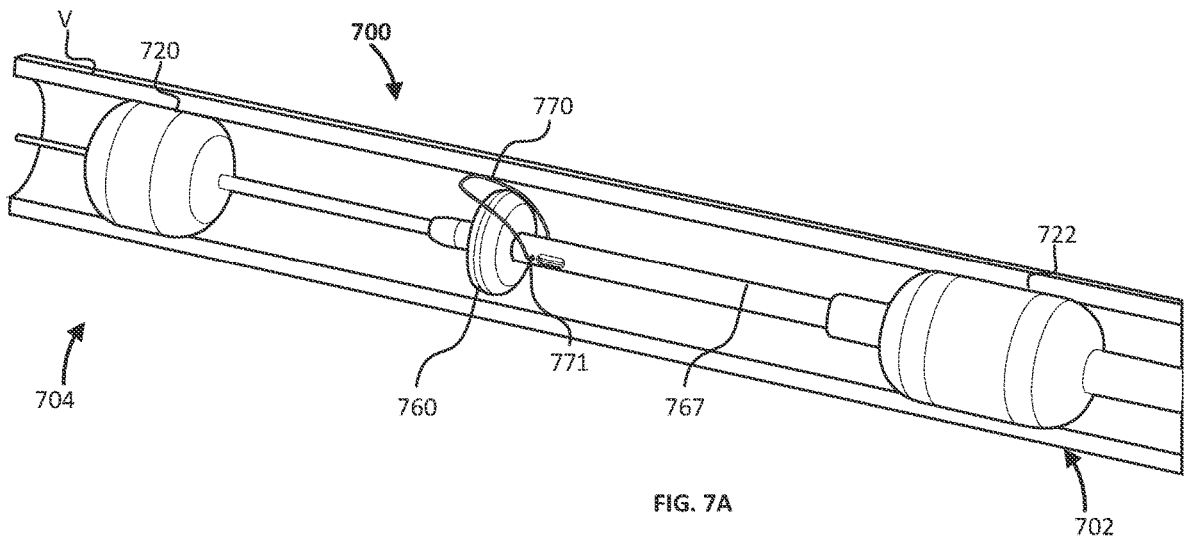
FIGS. 7A-C are schematic perspective and side detailed views of another embodiment of an agitating catheter having a hinge on an inflatable plug.
Figure 7B:
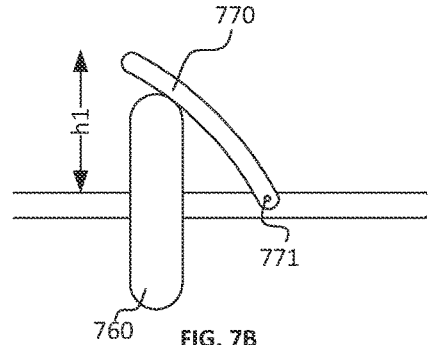
Figure 7C:
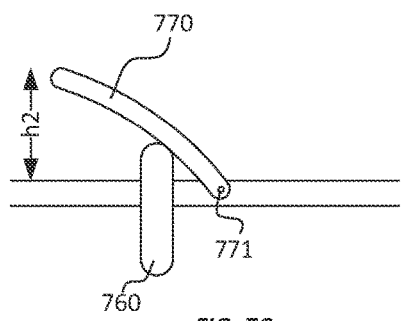

Another variation of a catheter is shown in FIGS. 6 and 7A-C. Like-numbered elements of FIGS. 6 and 7A-C will be easily identified as being similar to those elements of FIG. 1, except that such elements will be preceded with "6" or "7" instead of "4". Of note in catheter 600 of FIG. 6 is the inclusion of a plug 660 for agitating a blood clot. Plug 660 may be disk-shaped and may be formed of a rigid element to crush, loosen and/or agitate a blood clot. In at least some examples, plug 660 may be in the form of an inflatable element (e.g., a balloon) and may be in communication with a designated inflation tube 667. The catheter of FIGS. 7A-C is similar to that of FIG. 6 except that it also includes a hinged arm 770 that rests on plug 760 and is coupled to tube 767 at hinge 771. Because plug 760 is inflatable, its size may be altered. As shown in FIGS. 7B-C, by altering the size of plug 760, the height of hinged arm 770 may be changed from height h1 (FIG. 7B) to height h2 (FIG. 7C) or vice versa. In at least some examples, the height of the arm may be altered from being almost 0 (i.e., the arm is almost completely flat against tube 767) to a maximum height that is slightly smaller than the diameter of the target vessel. In this manner, the height of the arm may be chosen, and the arm may be used to agitate or loosen blood clots within the vessel.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

What is claimed is:

1. A device for removing a blood clot, the device extending between a proximal end and a distal end, the device comprising:

a central sheath having a sidewall and defining a plurality of apertures in the sidewall;

a first balloon adjacent the distal end;

a second balloon adjacent the proximal end; and at least two undulating wires disposed between the first balloon and the second balloon, the at least two undulating wires being coupled at one end to the central sheath, each of the at least two undulating wires having a free proximal end, and each of the at least two undulating wires having a plurality of peaks and valleys and being actuatable by manipulation of each free proximal end.

2. The device of claim 1, wherein each free proximal end extends through the central sheath out of the proximal end for direct manipulation by a physician.

3. The device of claim 1, wherein the at least two undulating wires are evenly distributed about a circumference of the central sheath.

4. The device of claim 1, wherein the plurality of apertures are disposed between ends of each of the at least two undulating wires.

5. The device of claim 1, wherein each of the at least two undulating wires is disposed to one side of the central sheath.

6. The device of claim 1, wherein each of the at least two undulating wires does not wrap around the central sheath.

7. The device of claim 1, wherein the at least two undulating wires comprise a shape memory material.

* * * * *